(12) United States Patent
Akiyama

(10) Patent No.: US 11,602,309 B2
(45) Date of Patent: Mar. 14, 2023

(54) NEEDLE MEMBER, SENSOR, AND METHOD FOR MANUFACTURING NEEDLE MEMBER

(71) Applicant: TERUMO KABUSHIKI KAISHA, Tokyo (JP)

(72) Inventor: Takeshi Akiyama, Chuo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 610 days.

(21) Appl. No.: 16/684,561

(22) Filed: Nov. 14, 2019

(65) Prior Publication Data

US 2020/0077957 A1  Mar. 12, 2020

Related U.S. Application Data

(63) Continuation of application No. PCT/JP2018/018182, filed on May 10, 2018.

(30) Foreign Application Priority Data

Jul. 5, 2017 (JP) .............................. JP2017-132115

(51) Int. Cl.
*A61B 5/00* (2006.01)
*A61B 5/145* (2006.01)
(Continued)

(52) U.S. Cl.
CPC .......... *A61B 5/6848* (2013.01); *A61B 5/1451* (2013.01); *A61B 5/1473* (2013.01); *B21G 1/08* (2013.01); *A61B 2562/12* (2013.01)

(58) Field of Classification Search
CPC ... A61B 5/6848; A61B 5/1451; A61B 5/1473; A61B 2562/12; A61B 5/14539;
(Continued)

(56) References Cited

U.S. PATENT DOCUMENTS 5,165,407 A    11/1992  Wilson et al.
5,669,543 A *  9/1997  Ueno .................... B65C 7/003
                                           112/222
(Continued)

FOREIGN PATENT DOCUMENTS

JP    H05-506172 A    9/1993
JP    H08-171349 A    7/1996
(Continued)

OTHER PUBLICATIONS

International Searching Authority, "International Search Report," issued in connection with International Patent Application No. PCT/JP2018/018182, dated Aug. 7, 2018.
(Continued)

*Primary Examiner* — Eric F Winakur
(74) *Attorney, Agent, or Firm* — Foley & Lardner LLP

(57) ABSTRACT

A needle member includes: a tubular side wall through which a hollow portion extends in a longitudinal direction. An opening portion connected to the hollow portion extends laterally through the tubular side wall. The tubular side wall comprises a side wall reinforcement portion located at a position opposing the opening portion, wherein the hollow portion is interposed between the opening portion and the side wall reinforcement portion.

5 Claims, 15 Drawing Sheets

(51) Int. Cl.
*A61B 5/1473* (2006.01)
*B21G 1/08* (2006.01)

(58) Field of Classification Search
CPC ............ A61B 5/14542; A61B 5/14514; A61B 5/14865; A61B 5/14532; B21G 1/08; B21C 37/0815; B21C 37/0822; B21C 37/157; B21C 37/185; B21D 17/02
See application file for complete search history.

(56) References Cited

U.S. PATENT DOCUMENTS

| | | | |
|---|---|---|---|
| 2004/0118902 A1* | 6/2004 | Adams | B21G 1/08 228/136 |
| 2005/0145677 A1* | 7/2005 | Ooyauchi | B21C 37/06 228/101 |
| 2008/0086041 A1 | 4/2008 | Heller et al. | |
| 2016/0338734 A1* | 11/2016 | Shah | A61M 5/3286 |

FOREIGN PATENT DOCUMENTS

| | | | | |
|---|---|---|---|---|
| JP | H11-173324 A | 6/1999 | | |
| JP | 2001-321439 A | 11/2001 | | |
| JP | 2003-190282 A | 7/2003 | | |
| JP | 2007-098109 A | 4/2007 | | |
| JP | 4499128 B2 | 7/2010 | | |
| WO | WO 91/15993 | * 10/1991 | ............... | A61B 5/00 |
| WO | WO-2015/114706 A1 | 8/2015 | | |
| WO | WO-2016/191302 A1 | 12/2016 | | |

OTHER PUBLICATIONS

International Searching Authority, "Written Opinion," issued in connection with International Patent Application No. PCT/JP2018/018182, dated Aug. 7, 2018.

International Searching Authority, International Search Report and Written Opinion issued in connection with International Patent Application No. PCT/JP2018/018182, dated Aug. 7, 2018.

* cited by examiner

NEEDLE MEMBER, SENSOR, AND METHOD FOR MANUFACTURING NEEDLE MEMBER

CROSS-REFERENCE TO RELATED APPLICATIONS

The present application is a bypass continuation of PCT Application No. PCT/JP2018/018182, filed on May 10, 2018, which claims priority to Japanese Application No. 2017-132115, filed on Jul. 5, 2017. The contents of these applications are hereby incorporated by reference in their entirety.

BACKGROUND

The present disclosure relates to a needle member, a sensor, and a method for manufacturing the needle member.

Conventionally, a technique of inserting or implanting a sensor inside a body of a subject such as a patient and detecting a substance to be measured (for example, glucose, pH, a physiologically active substance, protein, or the like) in a blood or a body fluid of the subject by the sensor has been conducted.

Japanese Patent No. 4499128 discloses an electrochemical sensor that is inserted and implanted into a patient using an insertion device and an insertion gun. In addition, PCT Publication No. WO 2016/191302 discloses a needle that can deliver a sensor percutaneously and in which a slot is formed.

SUMMARY

When the sensor is implanted in a body of a subject and performs detection of a substance to be measured for a predetermined period, such as one week, there is a case in which a needle member is only at the time of inserting a detection member, and there is a case in which the needle member and the detection member are used in the state of being implanted in the body together. In either case, it is preferable that the needle member have sufficient strength such that no impact occurs at the time of insertion and no bending or breakage occurs during the predetermined period in daily life. In addition, it is preferable that the needle member have a configuration in which the stress to the subject is reduced.

An object of the present disclosure is to provide a needle member having a configuration in which it is easy to secure a predetermined strength at a position of an opening portion even when the opening portion is formed in a tubular side wall, a sensor provided with the needle member, and a method for manufacturing the needle member.

According to a first embodiment of the present disclosure, a needle member defines a hollow portion, in which an opening portion connected to the hollow portion is formed in a tubular side wall, and a side wall reinforcement portion is formed at a position opposing the opening portion with the hollow portion interposed between the opening portion and the side wall reinforcement portion.

According to one aspect, the side wall reinforcement portion is a bent portion in which a part of the side wall is bent so as to protrude toward the hollow portion from a periphery in a circumferential direction.

According to one aspect, a blade surface portion having a blade surface inclined with respect to an extending direction is formed in a distal end portion, and the bent portion is not formed at a position of the blade surface portion in the extending direction but is formed at a position on a proximal end side of the blade surface portion.

According to one aspect, an opening reinforcement portion is provided at an edge portion, which defines the opening portion, of the side wall.

According to another embodiment of the present disclosure, a sensor includes: the above-described needle member; and a linear detection member located in the hollow portion of the needle member.

According to one aspect, a reinforcement portion inner surface, formed by the side wall reinforcement portion, of an inner surface of the needle member protrudes toward the hollow portion, and a receiving groove that receives the detection member is formed in the inner surface of the needle member at a position adjacent to the reinforcement portion inner surface in the circumferential direction of the needle member.

According to one aspect, the reinforcement portion inner surface includes: a top portion; and a side portion that is continuous from the top portion to one side of the needle member in the circumferential direction and in which a distance of the needle member in a radial direction from the top portion increases as being separated from the top portion toward the one side of the needle member in the circumferential direction, and the side portion forms a groove wall that defines the receiving groove, and the side portion forms a receiving surface that receives the detection member.

According to one aspect, an outer shape of a cross section of the detection member is substantially circular, and the receiving surface includes a concave curved surface capable of coming into surface-contact with a circumferential surface of the detection member.

According to another embodiment of the present disclosure, a sensor includes the above-described needle member, in which a detection unit capable of detecting a substance to be measured is integrated with an inner surface of the needle member.

According to another embodiment of the present disclosure, a method for manufacturing a needle member includes: a tubular body providing step of providing a tubular body having an opening portion formed in a side wall; and a bending pressing step of forming a bent portion that protrudes toward a hollow portion by pressing at a position, which opposes the opening portion in a radial direction of the tubular body, of the tubular body.

According to one aspect, the tubular body providing step includes: a concave portion formation step of forming a concave portion at an outer edge of a plate material; and a tubular shape pressing step of deforming the plate material into a tubular shape such that the outer edge where the concave portion is formed is aligned with another outer edge.

According to one aspect, the tubular body providing step further includes an opening reinforcement portion formation step of forming an opening reinforcement portion at an edge portion that defines the concave portion of the plate material.

Advantageous Effects of Invention

According to certain embodiments of the present disclosure, it is possible to provide a needle member having a configuration in which it is easy to secure the predetermined strength at the position of the opening portion even when the opening portion is formed in the tubular side wall, a sensor provided with the needle member, and a method for manufacturing the needle member.

DETAILED DESCRIPTION

Figure 1:
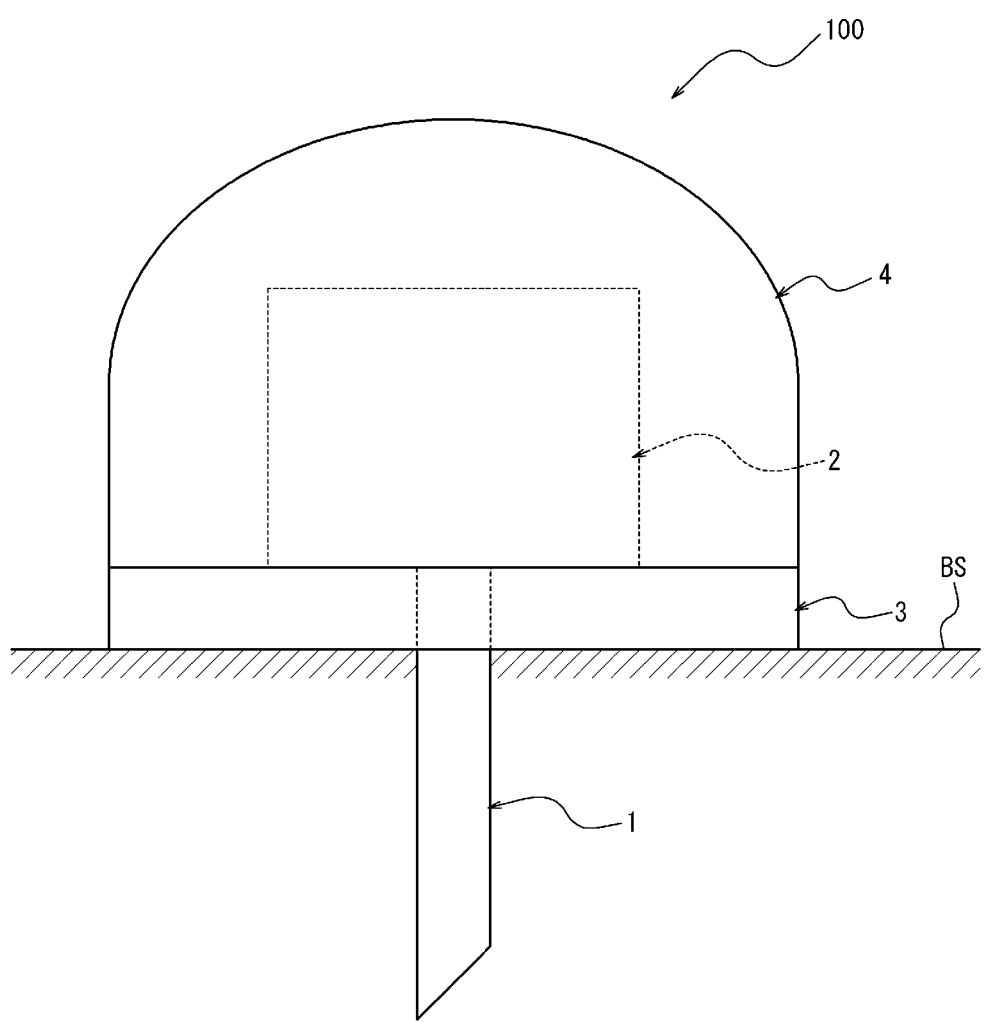
FIG. 1 is a view illustrating a measurement device including a sensor as one embodiment of the present invention.

Hereinafter, embodiments of a needle member, a sensor, and a method for manufacturing the needle member will be described with reference to FIGS. 1 to 17. The same reference numerals are used for common members and parts in the drawings.

FIG. 1 is a view illustrating a measurement device 100 including a sensor 1 as one embodiment. As illustrated in FIG. 1, the measurement device 100 includes the sensor 1, a control unit 2, a support member 3, and a housing 4.

The sensor 1 detects a substance to be measured (analyte), and transmits information on a detection result to the control unit 2. The control unit 2 is constituted by a processor, a memory, a battery, and the like. The control unit 2 analyzes a detection signal received from the sensor 1 and transmits an analysis result to an external device such as a display device as necessary. The support member 3 supports the sensor 1. Specifically, the support member 3 supports the sensor 1 by holding a proximal end portion of a needle member 10, which will be described later, of the sensor 1.

The housing 4 accommodates the control unit 2 therein, and is attached to the support member 3 in the state of covering the control unit 2.

The measurement device 100 is attached to a subject in a state where the sensor 1 has been inserted into a body. FIG. 1 illustrates a state where the control unit 2, the support member 3, and the housing 4 of the measurement device 100 are mounted on a body surface BS of the subject. The measurement device 100 measures the substance to be measured in a body fluid of the subject over time while being mounted on the subject. A period during which the measurement device 100 is mounted on the subject is appropriately defined by the determination of a doctor or the like to several hours, several days, one week, one month, or the like.

The substance to be measured is not particularly limited, and glucose, oxygen, pH, lactic acid, and the like in an interstitial fluid can be measured by selecting a detection member of the sensor.

In addition, the measurement device 100 illustrated in FIG. 1 may be configured to include an insertion mechanism that inserts the sensor 1 into the body. Alternatively, the insertion mechanism may be provided separately from the measurement device 100. In this case, the insertion mechanism may be configured to be detached from the measurement device 100 after the sensor 1 is inserted into the body.

Figure 2:
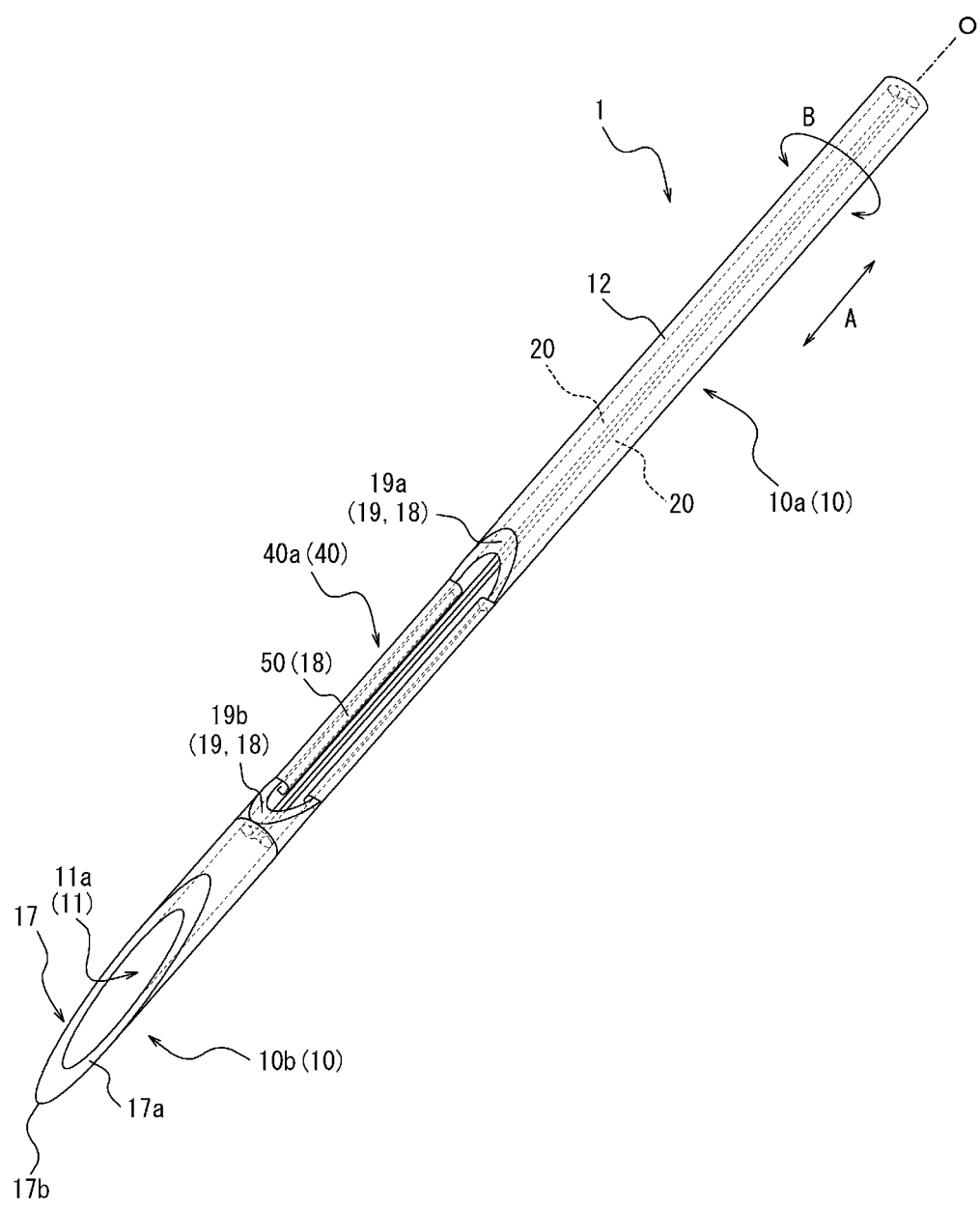
FIG. 2 is a perspective view illustrating a single sensor illustrated in FIG. 1.
Figure 3:
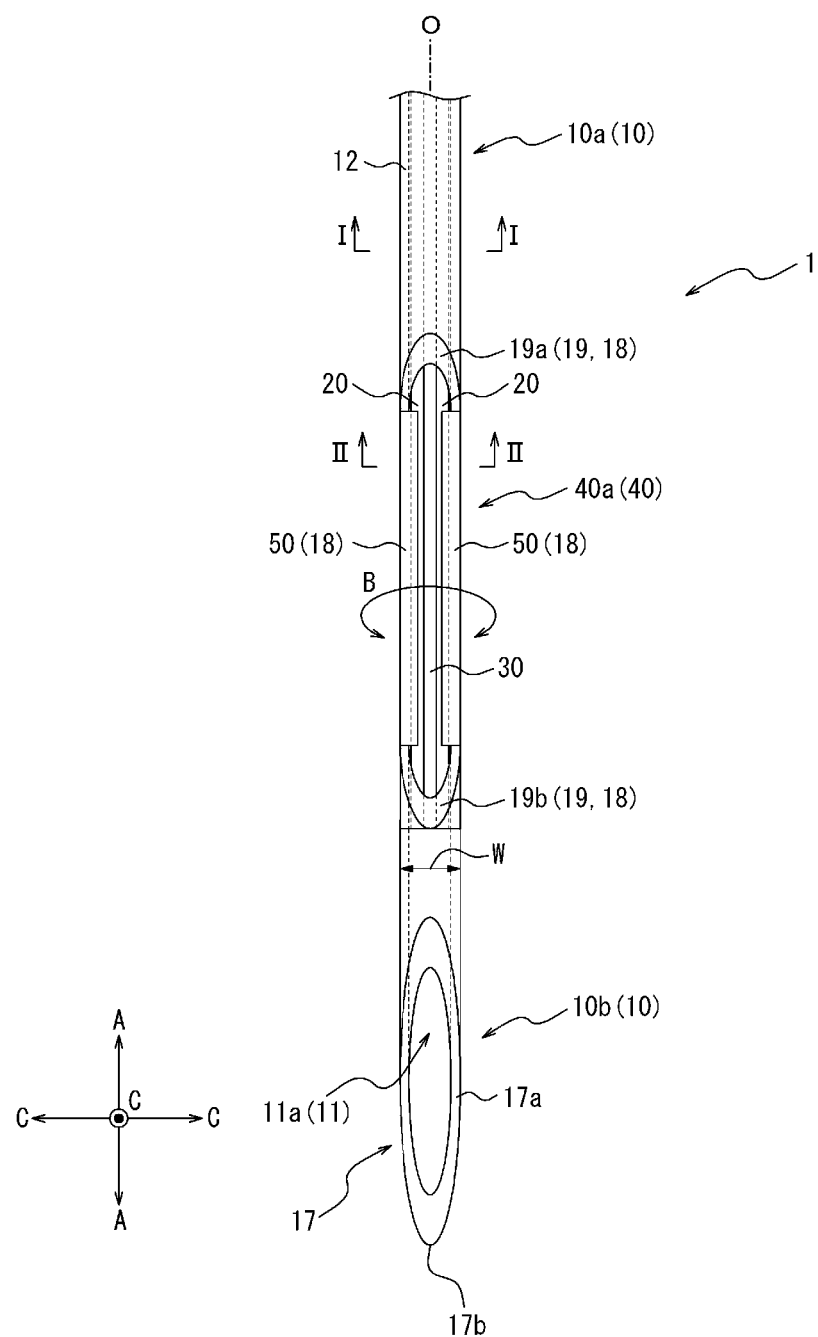
FIG. 3 is a front view of the single sensor illustrated in FIG. 1.
Figure 4:
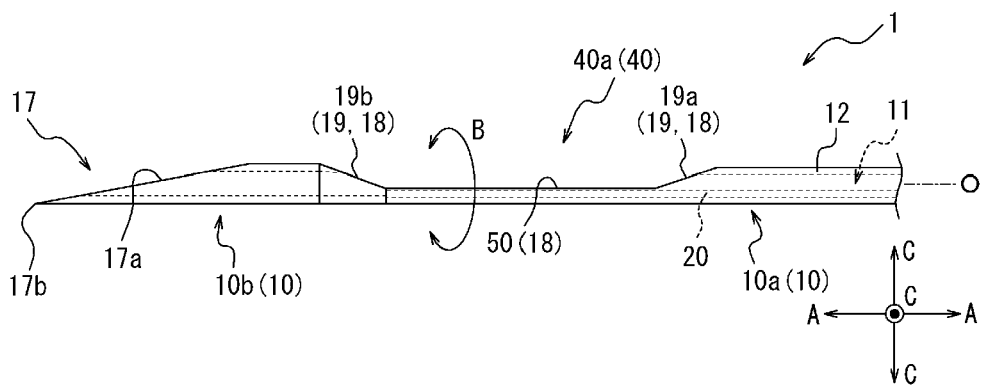
FIG. 4 is a side view of the single sensor illustrated in FIG. 1.
Figure 5:
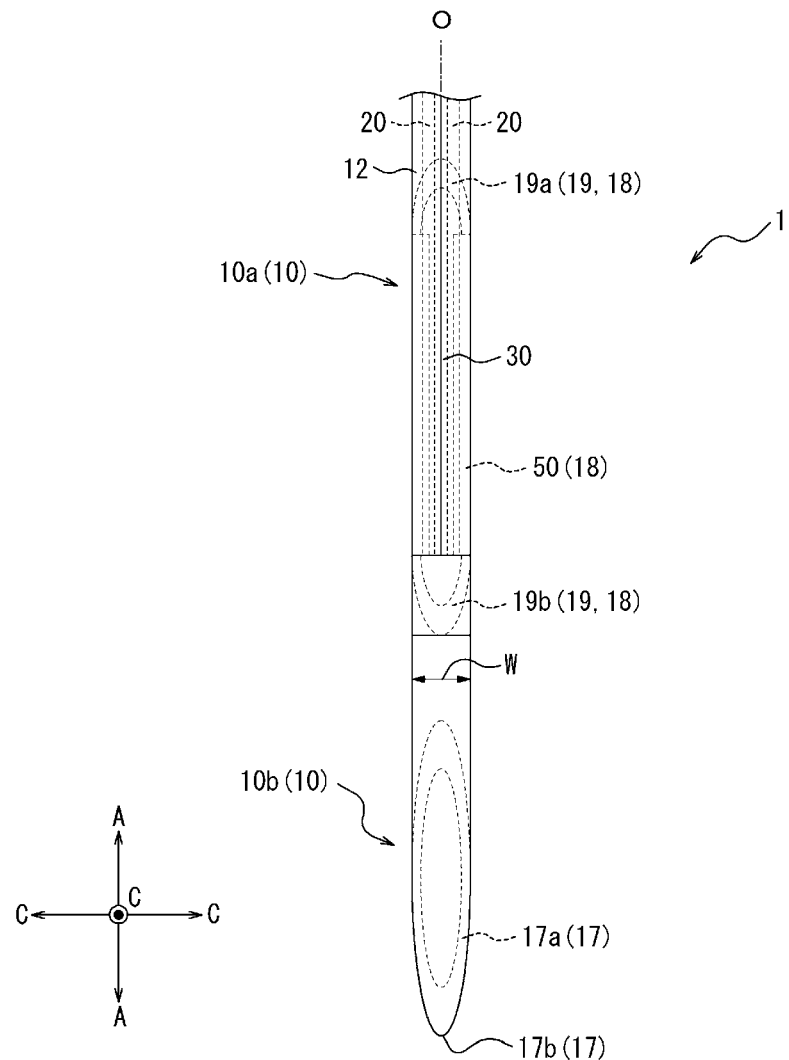
FIG. 5 is a back view of the single sensor illustrated in FIG. 1.
Figure 6:
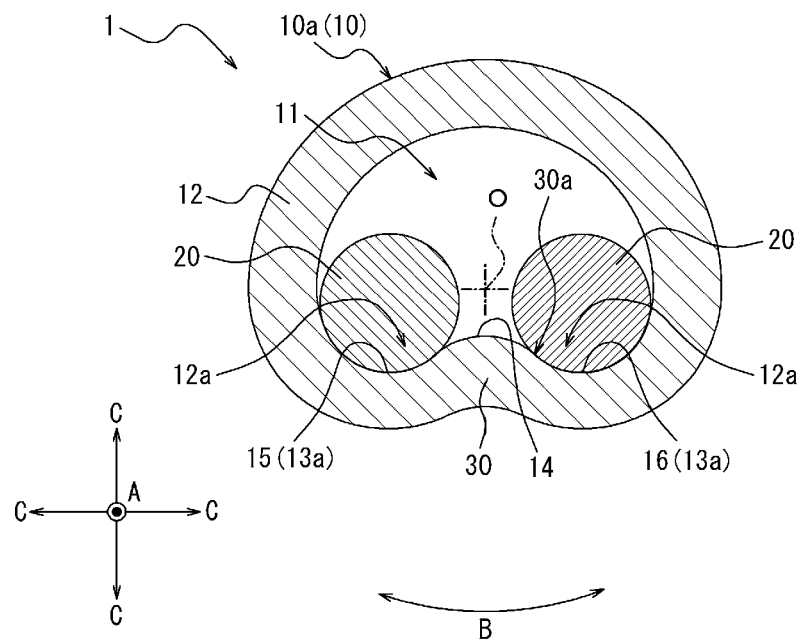
FIG. 6 is a cross-sectional view taken along line I-I in FIG. 3.
Figure 7:
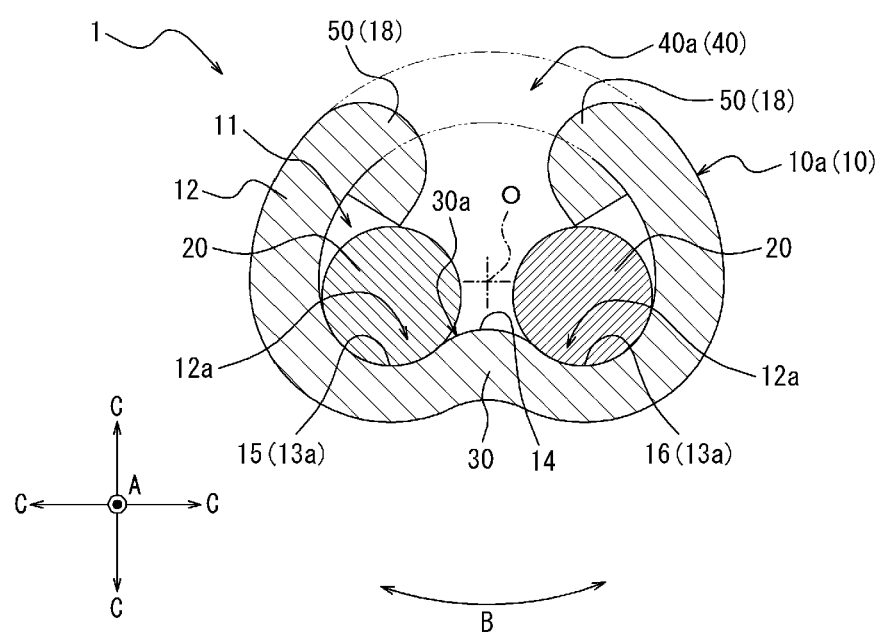
FIG. 7 is a cross-sectional view taken along line II-II in FIG. 3.
Figure 8:
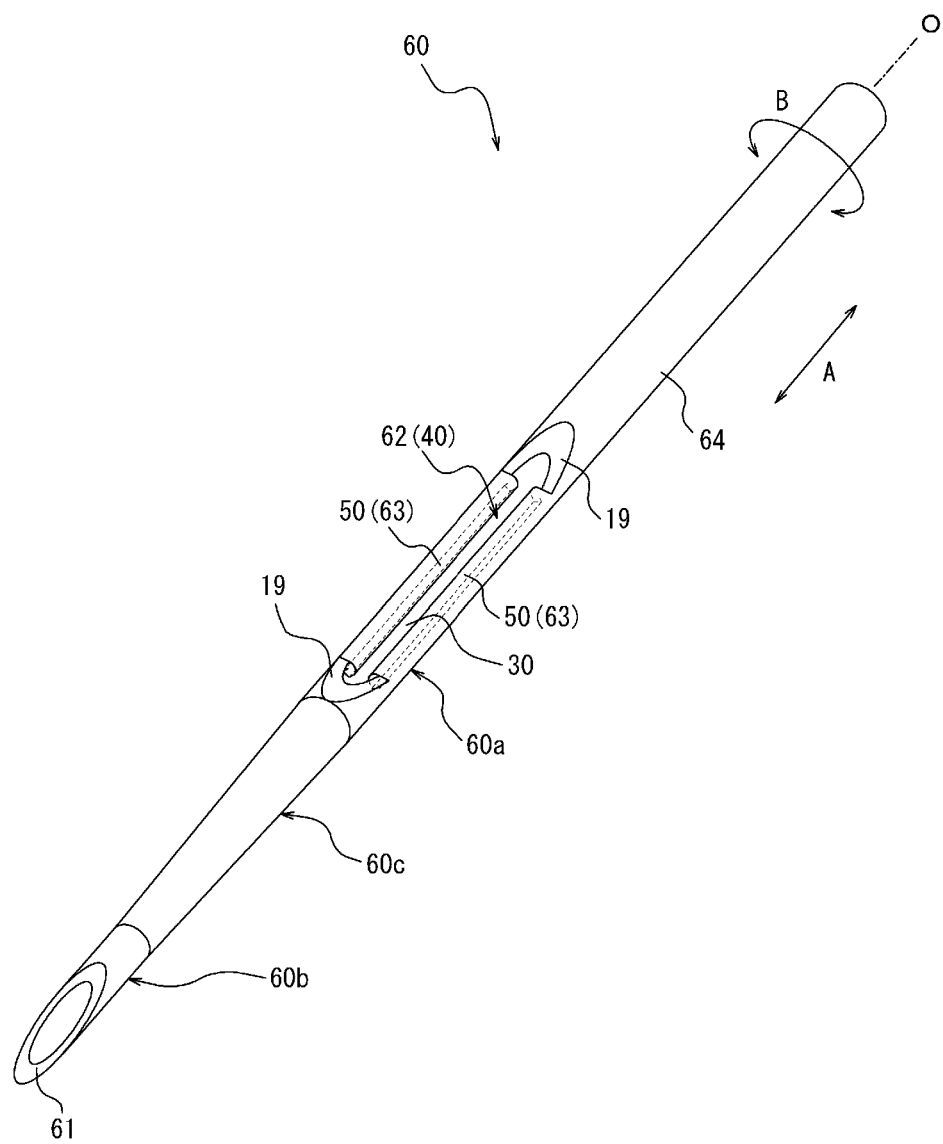
FIG. 8 is a perspective view illustrating a modification of a needle member in the sensor illustrated in FIG. 1.
Figure 9:
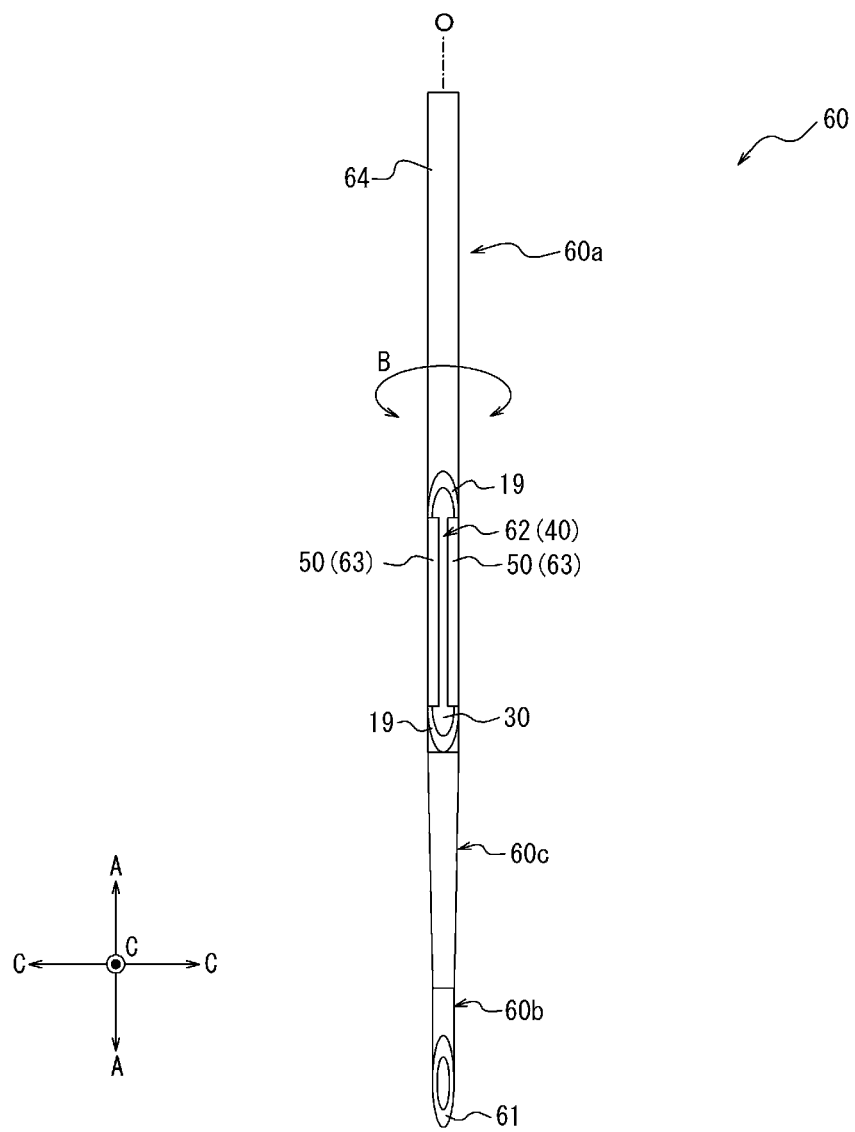
FIG. 9 is a front view of the needle member illustrated in FIG. 8.
Figure 10:
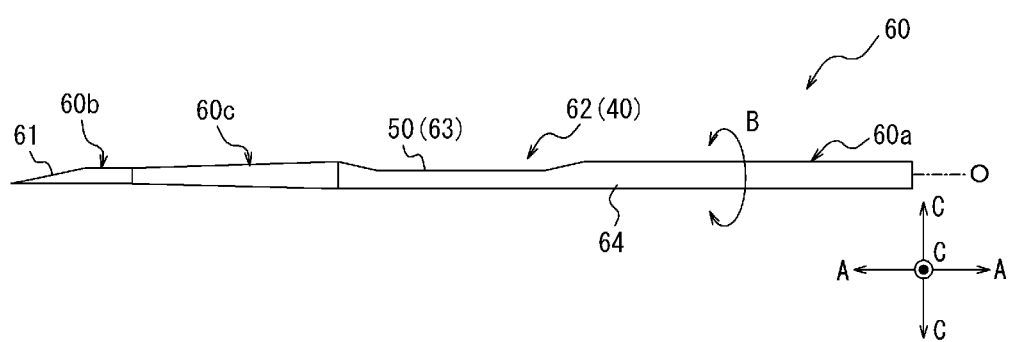
FIG. 10 is a side view of the needle member illustrated in FIG. 8.
Figure 11:
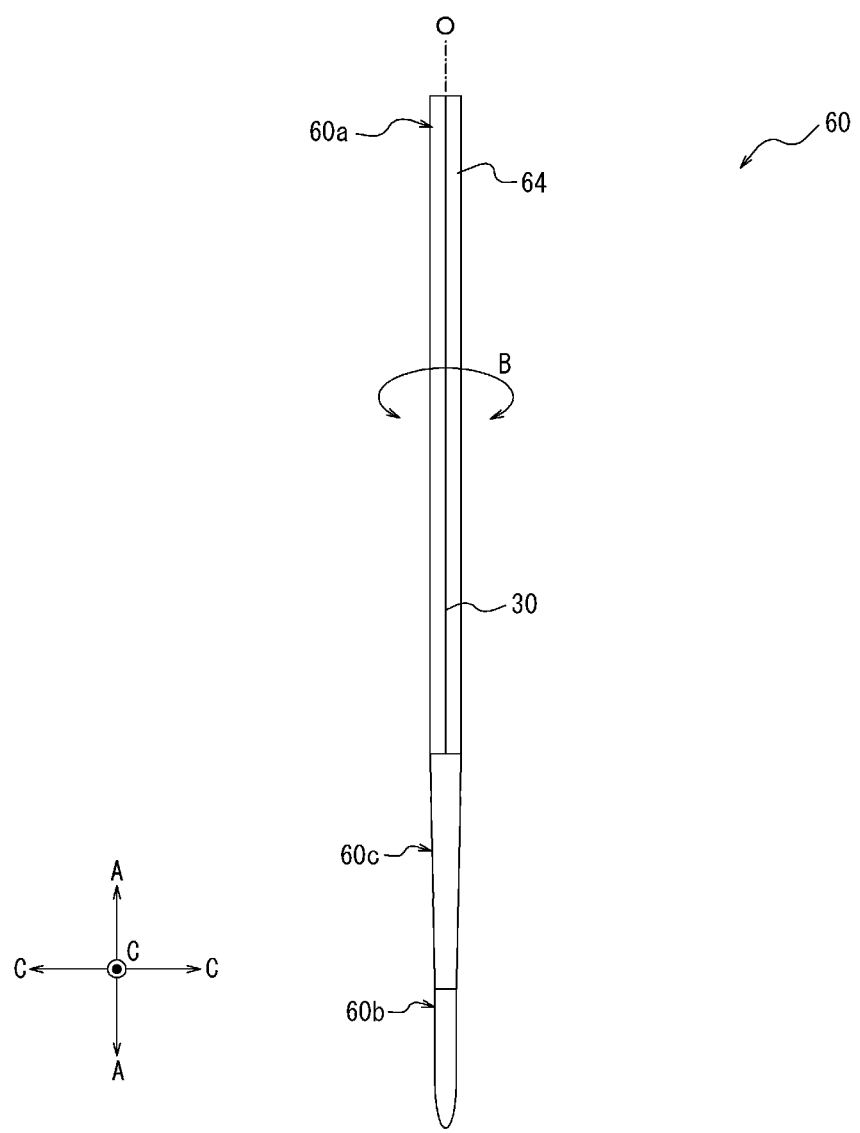
FIG. 11 is a back view of the needle member illustrated in FIG. 8.

Hereinafter, the sensor 1 of the present embodiment will be described. FIG. 2 is a perspective view illustrating the sensor 1. FIG. 3 is a front view of a portion on a distal end side of the sensor 1. FIG. 4 is a side view of the portion on the distal end side of the sensor 1. FIG. 5 is a back view of the portion on the distal end side of the sensor 1. FIG. 6 is a cross-sectional view taken along line I-I in FIG. 3. FIG. 7 is a cross-sectional view taken along line II-II in FIG. 3.

As illustrated in FIGS. 2 to 7, the sensor 1 includes the needle member 10 and a detection member 20.

The needle member 10 is a tubular hollow needle that defines a hollow portion 11 therein. A thickness of the needle member 10 is, for example, 0.5 mm to 0.2 mm in maximum diameter (corresponding to an outer diameter of 25 to 33 gauge), and a length thereof is 1 mm to 10 mm and preferably 3 to 6 mm. In addition, a wall thickness of the needle member 10 is set, for example, in the range of 0.02 mm to 0.15 mm. FIGS. 2 to 7 illustrate the substantially cylindrical needle member 10 having a maximum outer diameter of 0.3 mm (corresponding to an outer diameter of 29 gauge), a length of 9.5 mm, and a wall thickness of 0.05 mm.

As a material of the needle member 10, for example, a metal material, such as stainless steel, aluminum, an aluminum alloy, titanium, and a titanium alloy can be used. In the case of stainless steel, stainless steel conforming to SUS304, SUS304L, SUS321, and ISO 9626: 2016 defined in JIS G 4305: 2012 is preferable.

A through-hole 40a as an opening portion 40 connected to the hollow portion 11 is formed in a tubular side wall 12. The hollow portion 11 communicates with the outside of the needle member 10 through the through-hole 40a and a distal end opening 11a. Thus, the body fluid of the subject easily flows in and out of the needle member 10 as compared to the configuration without the opening portion 40. The body fluid in contact with the detection member 20 located inside the needle member 10 is also easily replaced. That is, it is possible to more accurately measure a temporal change of the substance to be measured by providing the opening portion 40.

In addition, a side wall reinforcement portion 30 is formed on the tubular side wall 12 at a position opposing the through-hole 40a as the opening portion 40 with the hollow portion 11 interposed therebetween as illustrated in FIG. 7. The side wall reinforcement portion 30 is formed on the tubular side wall 12 at a position opposite to the opening portion 40 with a longitudinal axis of the needle member 10 in a longitudinal direction interposed therebetween. Because the side wall reinforcement portion 30 is provided on the side wall opposite to the through-hole 40a, the strength of the needle member 10 can be reinforced at the position of the opening portion 40 in an extending direction A of the needle member 10 regardless of a shape and a length of the opening portion 40 even in the configuration in which the opening portion 40 is formed. That is, the opening portion 40 that has a desired shape and is formed in the side wall 12 can be realized while suppressing the reduction in strength of the needle member 10. The above-described "extending direction A of the needle member 10" means the longitudinal direction of the needle member 10.

The side wall reinforcement portion 30 is preferably provided over the entire region in which the opening portion 40 is provided in the extending direction A. In this manner, a point where the strength of the needle member 10 is locally small is barely formed in the region where the opening portion 40 is provided in the extending direction A.

Further, a gap is secured between the opening portion 40 and the detection member 20 in the hollow portion 11 in a cross-sectional view of the sensor 1 orthogonal to the extending direction A at the position of the opening portion 40 as illustrated in FIG. 7. In addition, the above gap communicates in the extending direction A inside the hollow portion 11 even other than the position of the opening portion 40 as illustrated in FIG. 6. That is, the body fluid having flown into the hollow portion 11 from the opening portion 40 can move in the extending direction A in the hollow portion 11 through the above-described gap in the hollow portion 11. As a result, it is easy to fill the periphery of the detection member 20 extending in the extending direction A inside the hollow portion 11 with the body fluid, and it is possible to promote the detection of the substance to be measured by the detection member 20.

Next, mode details of the side wall reinforcement portion 30 of the present embodiment will be described. The side wall reinforcement portion 30 of the present embodiment is a bent portion in which a part of the side wall 12 is bent so as to protrude toward the hollow portion 11 from the periphery of the needle member 10 in a circumferential direction B. Here, the "circumferential direction B of the needle member 10" means a direction along an outer surface of the needle member 10 in the cross section orthogonal to the extending direction A of the needle member 10. Because the side wall reinforcement portion 30 is formed into such a bent portion, the strength can be enhanced without providing another reinforcing member on the tubular side wall 12. In addition, even after forming a cylindrical side wall having a uniform wall thickness, the strength reinforcement can be realized by bending a part of the side wall by post-processing. Further, it is unnecessary to make the wall thickness of the side wall 12 before providing (before processing) the side wall reinforcement portion 30 thick in order for reinforcement, and to suppress an increase in diameter of the needle member 10. As a result, it is possible to suppress the pain felt by the subject during insertion and removal of the needle member 10 and during a period in which the needle member 10 is implanted. In addition, because the bent portion protrudes toward the hollow portion 11, the pain felt by the subject during the insertion and removal of the needle member 10 can be suppressed. The side wall 12 according to the present embodiment has a substantially uniform wall thickness regardless of a position in the circumferential direction B except for positions where an opening reinforcement portion 50, a slope portion 19, and a blade surface portion 17, which will be described later, are provided (see FIG. 6).

More specifically, the bent portion as the side wall reinforcement portion 30 in the present embodiment protrudes toward the through-hole 40a as the opening portion 40. That is, the side wall reinforcement portion 30 of the present embodiment is a bent portion in which a part of the side wall 12 is bent so as to project inward in the radial direction C of the needle member 10 relative to the circumference of the circumferential direction B of the needle member 10. The "radial direction C of the needle member 10" means a direction extending radially about the longitudinal axis O of the needle member 10 in a plane perpendicular to the extending direction A of the needle member 10. In addition, the "longitudinal axis O of the needle member 10" in the present embodiment is a longitudinal axis of a virtual cylinder in the needle member 10 specified by an outer surface of a portion excluding the bent portion as the side wall reinforcement portion 30. The extending direction A of the needle member 10 of the present embodiment described above substantially coincides with the axial direction of the longitudinal axis O. In addition, the circumferential direction B of the needle member 10 of the present embodiment described above substantially coincides with the circumferential direction having the longitudinal axis O as a longitudinal axis.

In addition, in other words, the reinforcement portion inner surface 30a, formed by the bent portion as the side wall reinforcement portion 30, of an inner surface of the needle member 10 of the present embodiment protrudes toward the hollow portion 11. Further, a receiving groove 12a, which accommodates and receives the linear detection member 20, is formed at a position adjacent to the reinforcement portion inner surface 30a in the circumferential direction B of the needle member on the inner surface of the needle member 10. That is, because the detection member 20 is received by the receiving groove 12a, it becomes easy to hold the detection member 20 in the hollow portion 11 at a fixed position, and it is possible to enhance position fixability in the hollow portion 11 of the detection member 20. Further, the receiving groove 12a is simultaneously formed by forming the bent portion as the side wall reinforcement portion 30 in the present embodiment. Thus, both strength reinforcement of the needle member 10 and improvement of the position fixability of the linear detection member 20 are realized with a simple configuration in which the bent portion is formed in the sensor 1 of the present embodiment.

The receiving grooves 12a receiving the separate detection members 20 are provided, respectively, on both sides adjacent to the reinforcement portion inner surface 30a in the circumferential direction B of the needle member 10 on the inner surface of the needle member 10 of the present embodiment.

The reinforcement portion inner surface 30a of the present embodiment will be described in more detail. The reinforcement portion inner surface 30a of the present embodiment includes: a top portion 14; and a first side portion 15 that is continuous from the top portion 14 to a side of the needle member 10 in the circumferential direction B and is away from the top portion 14 outward in the radial direction C of the needle member 10 as being separated from the top portion 14 toward the one side of the needle member 10 in the circumferential direction B; and a second side portion 16 that is continuous from the top portion 14 to another side of the needle member 10 in the circumferential direction B and is away from the top portion 14 outward in the radial direction C of the needle member 10 as being separated from the top portion 14 toward the other side of the needle member 10 in the circumferential direction B.

The top portion 14 protrudes toward the hollow portion 11. It is preferable that the top portion 14 be a substantially flat surface or a curved surface having a gently convex shape as in the present embodiment.

The first side portion 15 and the second side portion 16 are continuous with both ends of the top portion 14 in the circumferential direction B, respectively. The top portion 14 and the first side portion 15 may be gently continuous so as not to form a ridge line, and may be continuous such that a corner portion is formed by the ridge line. The same description also applies to the top portion 14 and the second side portion 16. However, it is preferable that the top portion 14 and the first side portion 15, and the top portion 14 and the second side portion 16 be more smoothly continuous using the curved surface so as not to form the ridge line as in the present embodiment. In this manner, when the detection member 20 is inserted into the hollow portion 11 from one end of the needle member 10, it is possible to reduce the possibility that the detection member 20 is damaged at the position where the top portion 14 and the first side portion 15 or the second side portion 16 are continuous.

The first side portion 15 forms a groove wall that defines one of the receiving grooves 12a, and the first side portion 15 forms a receiving surface 13a that receives one of the detection members 20 accommodated in the one receiving groove 12a. In addition, the second side portion 16 forms a groove wall that defines the other receiving groove 12a, and the second side portion 16 forms the receiving surface 13a that receives the second detection member 20 accommodated in the other receiving groove 12a. Because the side portion of the reinforcement portion inner surface 30a forms the receiving surface 13a in this manner, it is possible to further enhance the position fixability of the detection member 20 accommodated in the receiving groove 12a.

An outer shape of a cross section of the detection member 20 of the present embodiment is substantially circular as will be described later. In the present embodiment, each of the receiving surface 13a of the first side portion 15 and the receiving surface 13a of the second side portion 16 is provided with a concave curved surface that is capable of being in surface-contact with a circumferential surface of the detection member 20. With such a configuration, a contact area between the receiving surface 13a and the detection member 20 can be increased, and it is possible to further enhance the position fixability of the detection member 20.

Although the bent portion as the side wall reinforcement portion 30 of the present embodiment is provided in only one point in the circumferential direction B, it may be configured such that a plurality of bent portions are provided. For example, two bent portions as the side wall reinforcement portions 30 may be provided in the circumferential direction B, and three receiving grooves 12a may be formed to accommodate three detection members 20, respectively. In other words, the number of bent portions as the side wall reinforcement portions 30 can be set in accordance with the number of the detection members 20 arranged in the hollow portion 11.

In addition, each of the receiving grooves 12a of the present embodiment is configured to accommodate a single detection member 20, but may be configured to accommodate a plurality of detection members 20. However, when the plurality of detection members 20 are arranged in the single receiving groove 12a, there is a risk that the plurality of detection members 20 may be in contact with each other to be damaged. Thus, it is preferable that the plurality of detection members 20 be accommodated in the different receiving grooves 12a, respectively, in the state of being separated from each other as in the present embodiment. In the present embodiment, the configuration in which the two detection members 20 are accommodated in the different receiving grooves 12a, respectively, in the state of being separated from each other is realized by utilizing the bent portion as the side wall reinforcement portion 30.

Next, a formation position of the bent portion as the side wall reinforcement portion 30 in the extending direction A of the needle member 10 will be described. The needle member 10 includes a body portion 10a and a distal end portion 10b. The body portion 10a extends from the distal end portion 10b toward a proximal end side in the extending direction A. A blade surface portion 17, which includes a blade surface 17a inclined toward the distal end of the needle member 10, is formed in the distal end portion 10b of the needle member 10. The body portion 10a of the needle member 10 is provided with the side wall reinforcement portion 30. The bent portion as the side wall reinforcement portion 30 is not formed at a position overlapping with the blade surface portion 17 in the extending direction A. Further, the bent portion as the side wall reinforcement portion 30 is formed at a position on the proximal end side of the blade surface portion 17 in the extending direction A. Although the bent portion as the side wall reinforcement portion 30 is formed on a back surface (a lower surface of FIG. 4, that is, a surface on the same side as the blade tip 17b of the needle member 10) opposite to a front surface (an upper surface of FIG. 4) of the side wall 12 in a side view of the needle member 10 (see FIG. 4), the bent portion as the side wall reinforcement portion 30 is not formed on a back surface of the side wall 12 in a region where the blade surface portion 17 is formed in the extending direction A but is formed on the back surface of the side wall 12 in a region where the blade surface portion 17 is not formed in the extending direction A (see FIG. 5).

If the bent portion, as the side wall reinforcement portion 30, is not provided in the region where the blade surface portion 17 is formed in the extending direction A in this manner, the bent portion is less likely to be caught at the time of inserting the needle member 10 into the subject, and it is possible to mitigate the pain felt by the subject at the time of inserting the needle member 10.

As illustrated in FIGS. 2 to 7, the needle member 10 of the present embodiment has a configuration in which a maximum outer diameter of a cross section orthogonal to the extending direction A is substantially constant regardless of the position in the extending direction A. Specifically, a width W of the needle member 10 of the present embodiment in the front view (see FIG. 3) and the back view (see FIG. 5) is substantially constant regardless of the position in the extending direction A, and this width W is the maximum outer diameter of the cross section orthogonal to the extending direction A in the needle member 10 of the present embodiment. The needle member 10 of the present embodiment has a substantially cylindrical shape, but may have an elliptic cylinder such that an outer shape of the cross section has a flat shape. However, it is preferable to form the substantially cylindrical needle member 10 as in the present embodiment in order to reduce a piercing resistance at the time of inserting the needle member 10.

A needle member 60 illustrated in FIGS. 8 to 11 may be used instead of the needle member 10 of the present embodiment. The needle member 60 illustrated in FIGS. 8 to 11 is different from the above-described needle member 10 in terms that an outer diameter differs depending on a position in the extending direction A. Specifically, the needle member 60 includes: a body portion 60*a*; a distal end portion 60*b* that has a smaller outer diameter than the body portion 60*a* and in which a blade surface portion 61 is formed; and a tapered portion 60*c* that is located between the body portion 60*a* and the distal end portion 60*b* and whose outer diameter gradually decreases from the body portion 60*a* to the distal end portion 60*b* in the extending direction A. Further, a through-hole 62 as the opening portion 40 of the needle member 60 is formed at a position of the body portion 60*a*. A bent portion as the side wall reinforcement portion 30 is provided at least in a region opposing the opening portion 40 with respect to a longitudinal axis of the needle member 10 in the extending direction A. The bent portion as the side wall reinforcement portion 30 is preferably formed over the entire region of the body portion 60*a* in the extending direction A from the viewpoint of further enhancing the strength. At this time, the bent portion is not formed at a position of the distal end portion 60*b*. It is possible to efficiently reinforce the strength at the position of the opening portion 40 because the side wall reinforcement portion 60 is provided in the body portion 60*a*. Further, it is possible to mitigate a resistance at the time of puncturing and insertion because the side wall reinforcement portion 60 is not provided in the distal end portion 60*b*. The side wall reinforcement portion 30 may be formed to extend to the body portion 60*a* and the tapered portion 60*c*. The body portion 60*a* of the needle member 60 illustrated in FIGS. 8 to 11 has a substantially cylindrical shape excluding a portion where the through-hole 62 as the opening portion 40 is formed, a thickness thereof is 25 to 29 gauge and preferably 29 gauge (having an outer diameter of 0.3 mm), and a wall thickness thereof is 0.05 mm. In addition, the distal end portion 60*b* of the needle member 60 illustrated in FIGS. 8 to 11 also has a substantially cylindrical shape excluding a portion where the blade surface portion 61 is formed, a thickness thereof is 25-33 gauge and preferably 33 gauge (having an outer diameter of 0.2 mm), and a wall thickness thereof is 0.03 mm.

Next, the opening reinforcement portion 50 of the needle member 10 illustrated in FIGS. 2 to 7 will be described. As illustrated in FIG. 7, the opening reinforcement portion 50 that is formed to be bent toward the hollow portion 11 is provided at an edge portion 18, which defines the through-hole 40*a* as the opening portion 40, of the side wall 12. Specifically, the opening reinforcement portions 50 of the present embodiment are respectively formed in the edge portions 18 on both sides in the circumferential direction B with respect to the through-hole 40*a* as the opening portion 40. More specifically, the side wall 12 of the present embodiment is formed of a plate material, and the plate material is bent toward the hollow portion 11 at positions on both the sides in the circumferential direction B of the through-hole 40*a*. In other words, the plate material forming the side wall 12 of the present embodiment is folded to be superimposed at the positions on both the sides in the circumferential direction B of the through-hole 40*a*, and the opening reinforcement portions 50 are configured using such bent and stacked portions that have been folded to be stacked. That is, the edge portion 18 defining the through-hole 40*a* is made thicker than the periphery in the circumferential direction B due to the bent and stacked portion, and as a result, it is possible to enhance the strength of the edge portion 18 of the through-hole 40*a* as the opening portion 40.

Further, portions, positioned on both sides in the extending direction A of the needle member 10, of the edge portions 18 defining the through-hole 40*a* as the opening portion 40 are formed of the slope portions 19 inclined with respect to the extending direction A. Specifically, the edge portion 18 on the proximal end side in the extending direction A with respect to the through-hole 40*a* is formed of a first slope portion 19*a* inclined so as to approach the longitudinal axis O as proceeding toward the distal end side in the extending direction A. In addition, the edge portion 18 on the distal end side in the extending direction A with respect to the through-hole 40*a* is formed of a second slope portion 19*b* inclined so as to be away from the longitudinal axis O as proceeding toward the distal end side in the extending direction A. Because the edge portions 18 on both the sides in the extending direction A of the through-hole 40*a* as the opening portion 40 are formed of the above-described slope portions 19 in this manner, it is possible to reduce the piercing resistance at the time of inserting or removing the needle member 10 into or from the subject as compared to the case where the same positions are formed using surfaces orthogonal to the extending direction A. In particular, the first slope portion 19*a* and the second slope portion 19*b* contribute to the reduction of the piercing resistance both the insertion and the removal of the needle member 10. That is, the first slope portion 19*a* and the second slope portion 19*b* can reduce the pain accompanying a change in diameter of the needle member 10 and hooking during the insertion and removal in a skin insertion site of the subject.

Even in the needle member 60 as the modification described above (see FIGS. 8 to 11), the opening reinforcement portion 50 and the slope portion 19 are provided at an edge portion 63 defining the through-hole 62 as the opening portion 40 similarly to the needle member 10. The side wall 64 of the needle member 60 has a substantially uniform wall thickness regardless of the position in the circumferential direction B excluding positions where the opening reinforcement portion 50, the slope portion 19, and the blade surface portion 61 are provided.

Figure 12:
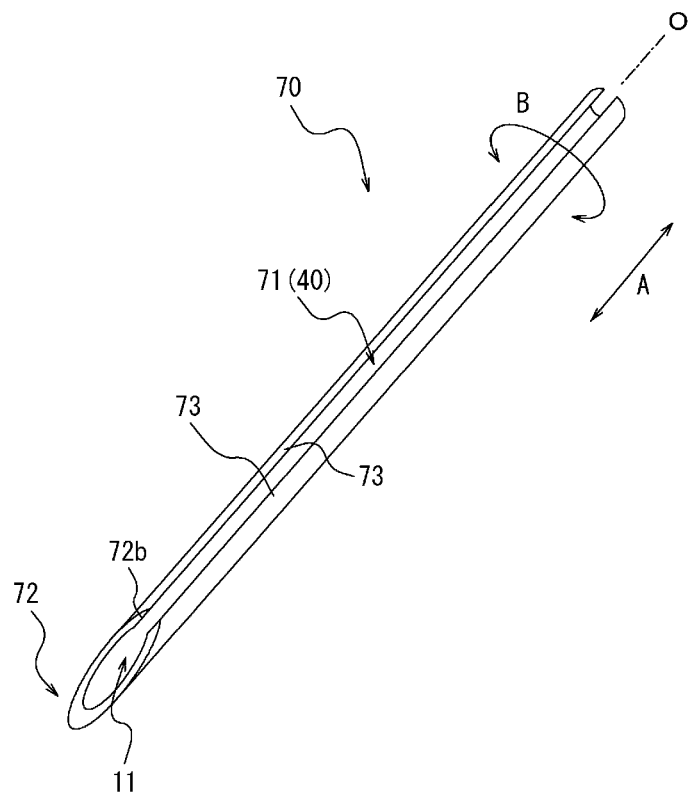
FIG. 12 is a perspective view illustrating a modification of the needle member in the sensor illustrated in FIG. 1.
Figure 13:
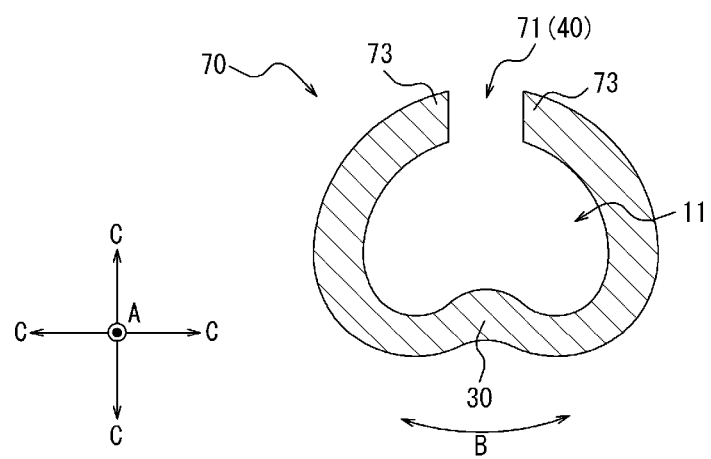
FIG. 13 is a cross-sectional view at a position of an opening portion of the needle member illustrated in FIG. 12.

In addition, the opening portions 40 of the needle member 10 illustrated in FIGS. 2 to 7 and the needle member 60 illustrated in FIGS. 8 to 11 are both the through-holes (the through-hole 40*a* in FIGS. 2 to 7 and the through-hole 62 in FIGS. 8 to 11), but the opening portion 40 may be configured using a slit 71 extending to a distal end of a needle member 70 in the extending direction A of the needle member 70 as in the needle member 70 as another modification of the needle member 10 illustrated in FIGS. 12 and 13. If the needle member 70 provided with the slit 71 extending to the distal end in the extending direction A is used, it is possible to remove the needle member 70 without passing through a connection point between the detection member 20 and the control unit 2 after inserting the detection member 20 into the body of the subject. That is, the needle member 70 can be used as an insertion needle that inserts only the detection member 20 into the living body.

As illustrated in FIGS. 12 and 13, it is preferable that a position of the slit 71 as the opening portion 40 in the circumferential direction B be substantially equal to a position of a heel portion 72*b* of a blade surface portion 72 in the circumferential direction B. In other words, it is preferable to provide the slit 71 as the opening portion 40 at the position of the heel portion 72b of the blade surface portion 72. In this manner, the blade surface portion 72 and the slit 71 as the opening portion 40 can be arranged at different positions in the extending direction A, and it is possible to realize a configuration in which a bent portion as the side wall reinforcement portion 30 is not formed at the position of the blade surface portion 72 in the extending direction A even if the bent portion as the side wall reinforcement portion 30 is provided in the entire region of the position opposing the slit 71 as the opening portion 40 with the hollow portion 11 interposed therebetween. That is, even if the entire region at the position opposing the slit 71 as the opening portion 40 with the hollow portion 11 interposed therebetween is reinforced by the bent portion as the side wall reinforcement portion 30, it is possible to suppress an increase in piercing resistance at the time of insertion and removal of the needle member 70 because the bent portion is not formed at a position overlapping with the blade surface portion 72 in the extending direction A.

Although the opening reinforcement portion 50 provided in the needle member 10 and the needle member 60 described above is not provided at an edge portion 73 defining the slit 71 in the needle member 70 illustrated in FIGS. 12 and 13, the opening reinforcement portion 50 similar to the above-described one may be provided. Here, the "tubular shape" in the present embodiment also includes a true circular shape or an elliptical shape. In addition, the "tubular shape" in the present embodiment is a meaning that include not limited to an endless configuration but also a shape, for example, a C-shaped cross-sectional shape as illustrated in FIGS. 12 and 13, that does not form a closed complete ring due to presence of a gap such as a slit extending over the entire region in the extending direction of the needle member.

In this manner, the needle member 60 illustrated in FIGS. 8 to 11 or the needle member 70 illustrated in FIGS. 12 and 13 may be used, instead of the needle member 10 of the sensor 1.

The detection member 20 is a linear member located in the hollow portion 11 of the needle member 10. As the detection member 20, a member that detects an electrical signal according to the amount or concentration of a substance to be measured can be used. The detection member 20 extends in the hollow portion 11 along the extending direction A of the needle member 10.

Specifically, the detection member 20 of the present embodiment is a wire electrode having a circular cross-sectional shape. As illustrated in FIGS. 2 to 7, the wire electrodes as the two detection members 20 are accommodated in the receiving grooves 12a of the hollow portion 11 in the present embodiment. More specifically, a first detection member 20 is accommodated in one of the receiving grooves 12a where the first side portion 15 forms the receiving surface 13a. A second detection member 20 is accommodated in the other receiving groove 12a where the second side portion 16 forms the receiving surface 13a. An outer diameter of the wire electrode as the detection member 20 of the present embodiment is 0.02 mm to 0.2 mm.

The first detection member 20 includes: a detection unit configured using a conductive core material as a base to detect the substance to be measured on an outer wall of the core material; and a protective portion obtained by coating the top of the outer wall of the core material with an insulating material. The detection unit is a working electrode that detects a change in electrical characteristics of the substance to be measured, and is formed on the surface of the core material using a thin film forming means such as dipping, electrolytic polymerization, and sputtering. In the present embodiment, the second detection member 20 constitutes a reference electrode with respect to the working electrode as the above-described detection unit. Three detection members 20 may be arranged in the hollow portion 11, and the working electrode, the reference electrode, and a counter electrode may be constituted by the three detection members 20, respectively. In addition, the needle member 10 may be used as the reference electrode or the counter electrode.

In addition, a connection portion that penetrates through the support member 3 and is connected to the control unit 2 is provided at a proximal end portion of the detection member 20 of the present embodiment. Information on the substance to be measured detected by the detection unit is transmitted to the control unit 2 via the connection portion.

Although the linear detection member 20 as a separate body from the needle member 10 is used in the sensor 1 of the present embodiment, it may be configured such that a detection unit capable of detecting a substance to be measured is integrated with an inner surface of the needle member 10 by etching or the like, instead of the linear detection member 20. Examples of the configuration in which the detection unit is integrated with the inner surface of the needle member 10 include a configuration in which an electrode layer or a reagent layer serving as the detection unit is stacked on the inner surface of the needle member 10.

Further, a fixing member that fixes the position of the detection member 20 with respect to the needle member 10 may be provided at the position of the proximal end portion of the needle member 10. The fixing member can be made of, for example, a fixing material such as an adhesive. If such a fixing member is used, the position of the detection member 20 with respect to the needle member 10 can be fixed at the proximal end portion of the needle member 10. Even when the fixing member is provided at the proximal end portion of the needle member 10, a portion of the detection member 20 located on the distal end side of the proximal end portion of the needle member 10 can move in the radial direction C of the needle member 10, but the needle member 10 of the present embodiment is provided with the above-described receiving groove 12a, and thus, it is also difficult to move the portion of the detection member 20 located on the distal end side of the needle member 10. The fixing member is not limited to the above-described example made of the fixing material such as the adhesive, and may be a fixing member, for example, configured using an elastic material such as rubber that is locked by the needle member 10 by being pinched and supported by the needle member 10.

Figure 14:
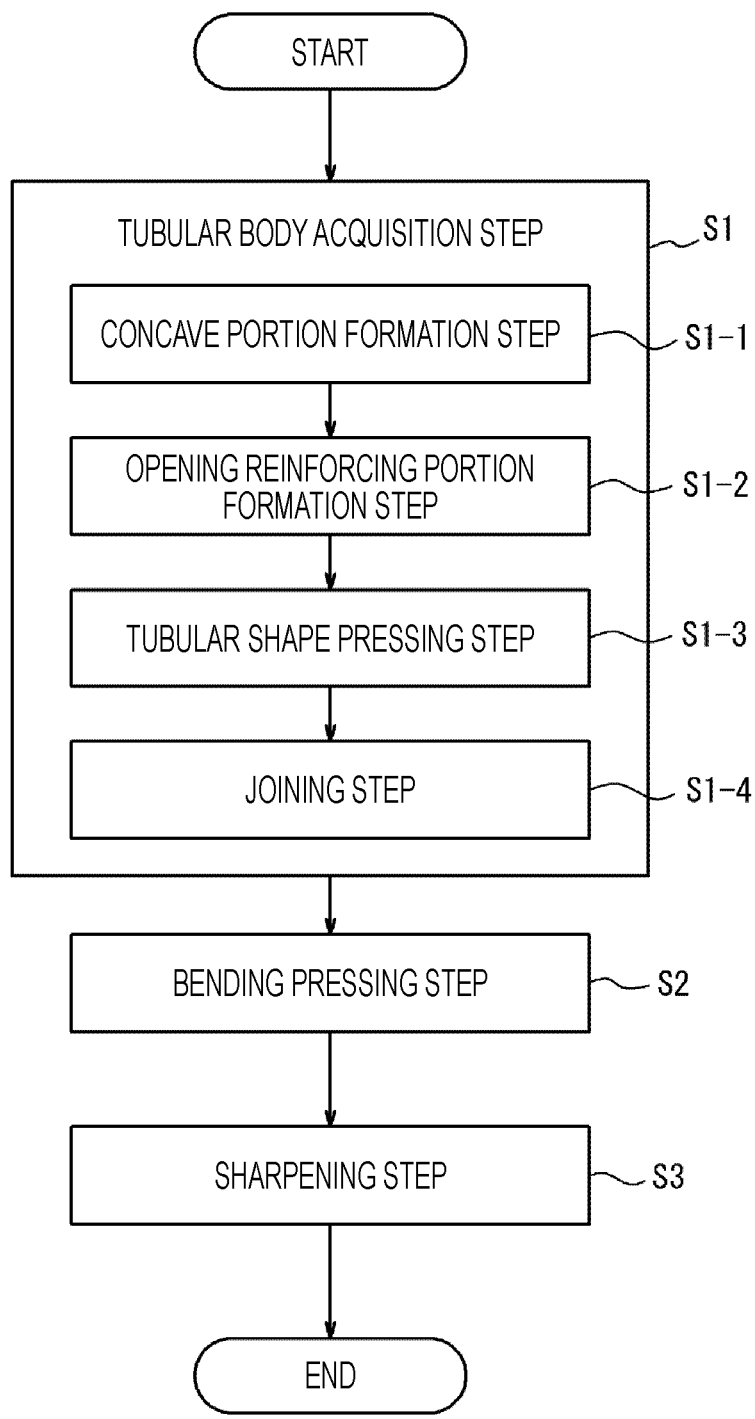
FIG. 14 is a flowchart illustrating an example of a method for manufacturing the needle member in the sensor illustrated in FIG. 1.
Figure 15A:
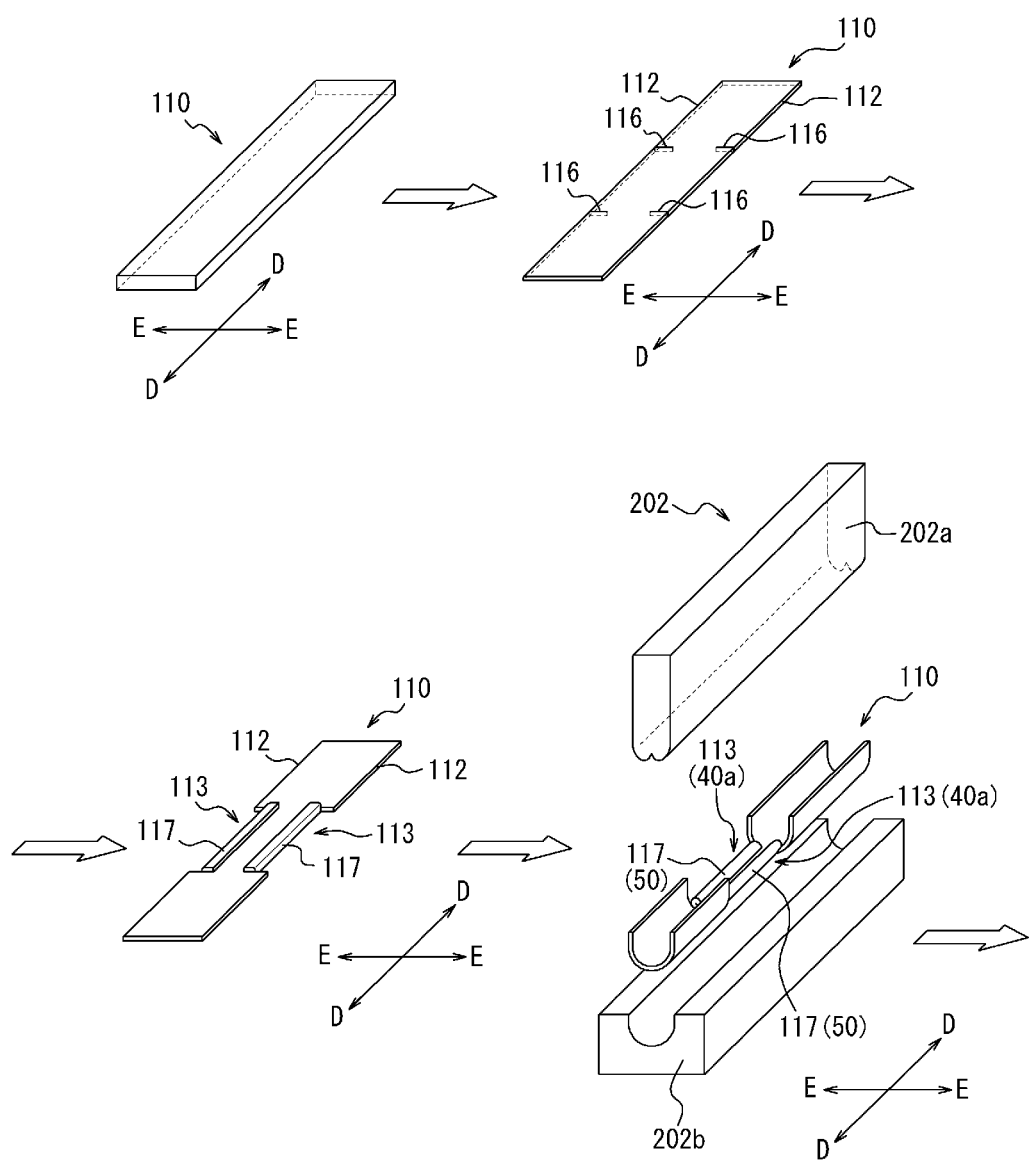
FIG. 15A is a schematic view illustrating an outline of a part of a series of steps illustrated in FIG. 14.
Figure 15B:
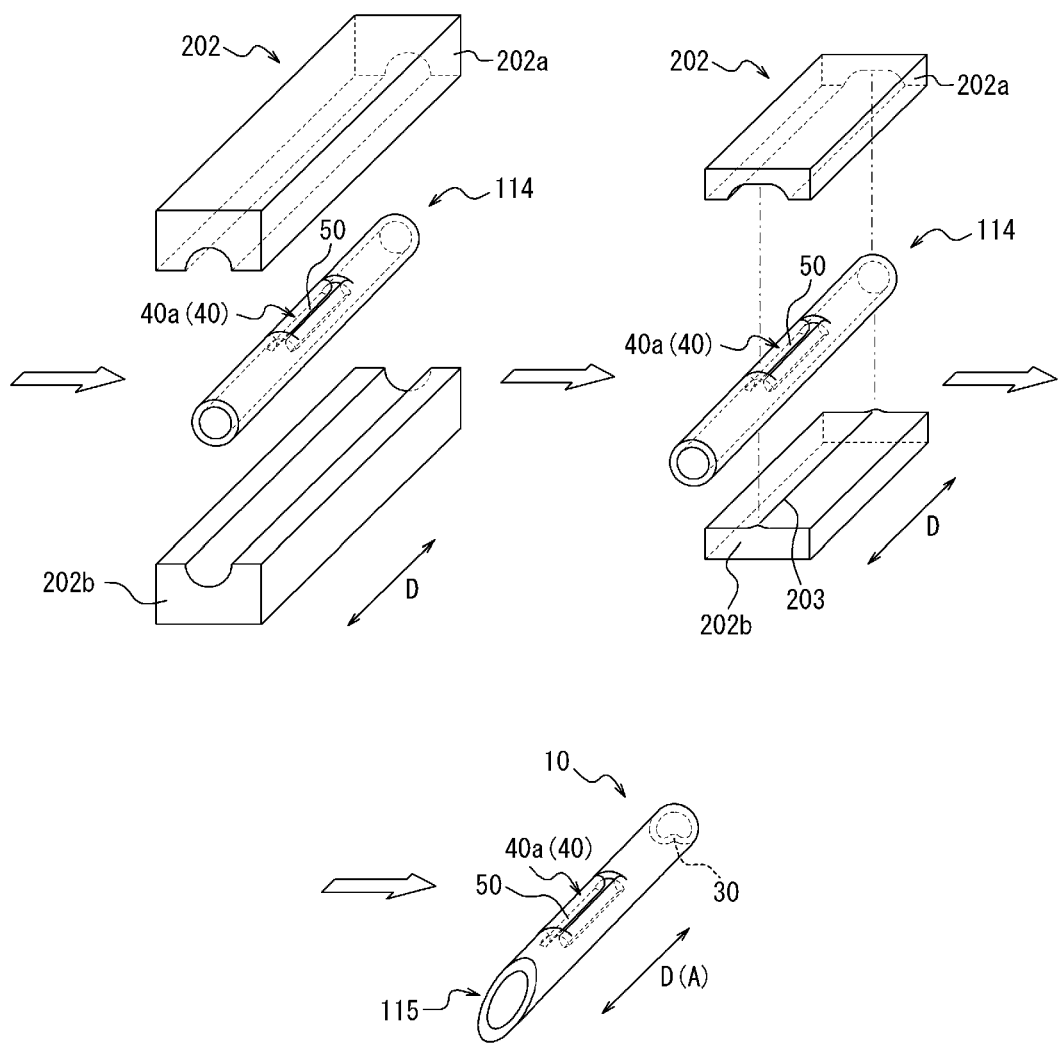
FIG. 15B is a schematic view illustrating an outline of a part of the series of steps illustrated in FIG. 14.

Next, a method for manufacturing the needle member 10 in the sensor 1 will be described. FIG. 14 is a flowchart illustrating an example of the method for manufacturing the needle member 10, and FIGS. 15A and 15B are schematic views illustrating outlines of a series of steps illustrated in FIG. 14. The method for manufacturing the needle member 10 illustrated in FIGS. 14, 15A and 15B includes: a tubular body providing step S1 of providing a tubular body 114 having an opening portion 40 formed in a side wall; a bending pressing step S2 of forming a bent portion protruding toward a hollow portion by pressing at a position, which opposes the opening portion 40 in the radial direction C of the tubular body 114, of the tubular body 114; and a sharpening step S3 of forming a blade surface portion 115 at one end portion of the tubular body 114.

In addition, the tubular body providing step S1 includes: a concave portion formation step S1-1 of forming a concave portion 113 in an outer edge 112 of a plate material 110; an opening reinforcement portion formation step S1-2 of forming an opening reinforcement portion at an edge portion that defines the concave portion 113 of the plate material 110; a tubular shape pressing step S1-3 of deforming the plate material 110 into a tubular shape such that the outer edge where the concave portion 113 is formed is aligned with another outer edge; and a joining step S1-4 of welding or bonding a portion of a joint X of the plate material 110 deformed into the tubular shape in the tubular shape pressing step S1-3 as illustrated in FIG. 14.

Figure 16:
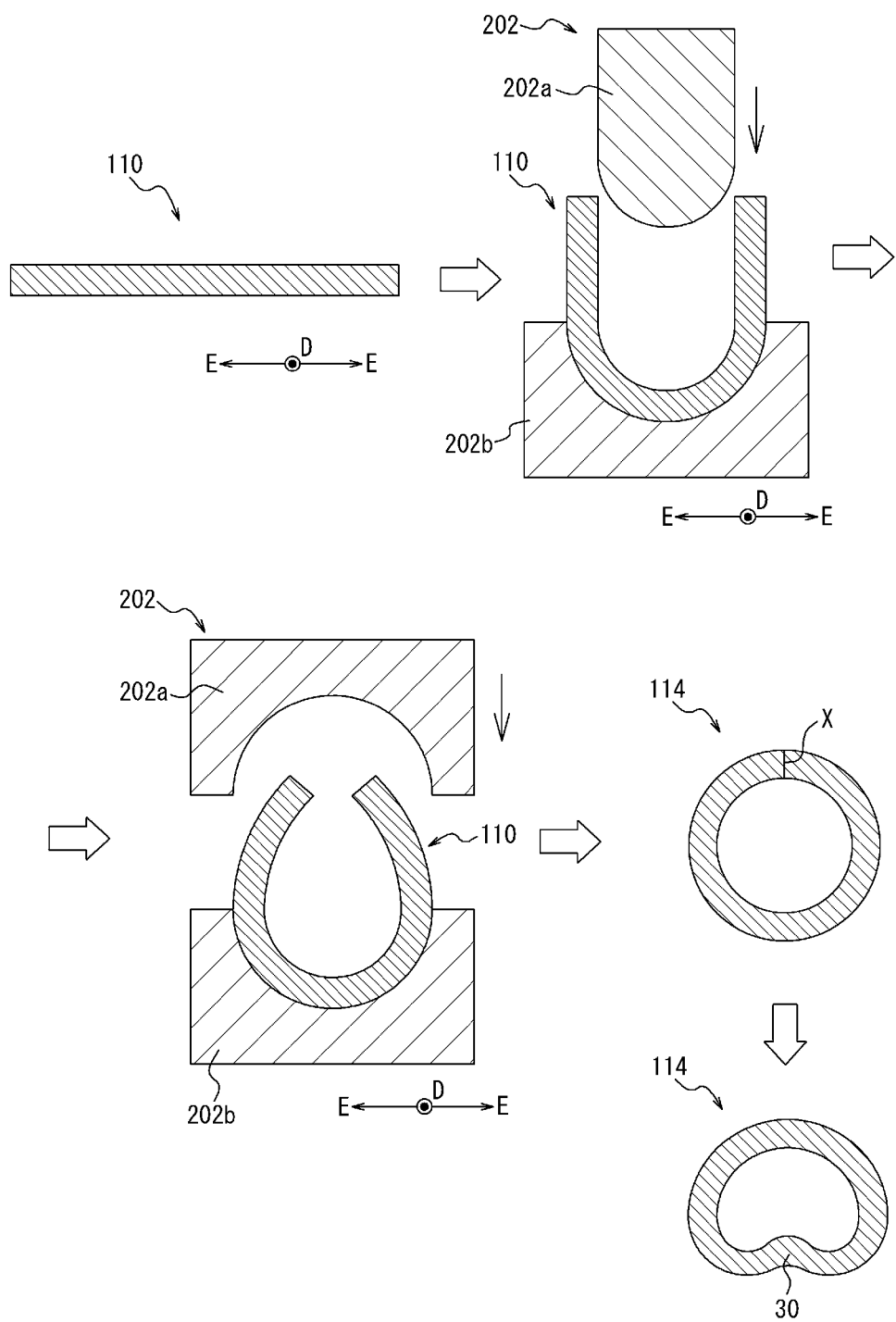
FIG. 16 is a view illustrating a temporal change of a cross-sectional shape of a material to be pressed that is subjected to pressing in the series of steps of FIG. 14.

FIG. 16 is a view illustrating a temporal change of a cross-sectional shape of a material to be pressed that is subjected to pressing in the series of steps S1 to S3 of FIGS. 14, 15A, and 15B. Hereinafter, the respective steps S1 to S3 in FIG. 14 will be described in detail with reference to FIGS. 15A, 15B, and 16. White arrows in FIGS. 15A, 15B, and 16 represent a temporal change in the steps. Specifically, an outline of the tubular body providing step S1 is illustrated in all the drawings of FIG. 15A, a drawing depicted on the left of the upper part of FIG. 15B, and drawings depicted on the upper and middle parts of FIG. 16. An outline of the bending pressing step S2 is illustrated in a drawing depicted on the right of the upper part of FIG. 15B and a drawing depicted on the lower part of FIG. 16. An outline of the sharpening step S3 is illustrated in a drawing on the lower part of FIG. 15B.

First, the tubular body providing step S1 of the present embodiment will be described. As illustrated in the drawing depicted on the right of the upper part of FIG. 15A and the drawing depicted on the left of the lower part of FIG. 15A, a plurality of notches 116 corresponding to a width of the above-described opening reinforcement portion 50 (see FIG. 2 and the like) in the extending direction A (the same direction as the longitudinal direction D of the plate material 110) are formed, respectively, at the linear outer edges 112 on both the sides of the rectangular plate material 110 in a lateral direction E in the concave portion formation step S1-1 of the tubular body providing step S1 of the present embodiment. At this time, at least two or more pairs of notches are formed as the plurality of notches 116. Further, a portion between the adjacent notches 116 in each of the outer edges 112 is folded toward one side of the plate material 110 in a thickness direction to form a bending piece 117. The concave portion 113 is formed in the outer edge 112 by folding the bending piece 117. When the needle member 10 is completed, the concave portion 113 serves as the through-hole 40a (see FIG. 2 and the like) as the opening portion 40 described above.

In addition, the opening reinforcement portion formation step S1-2 of the tubular body providing step S1 of the present embodiment is executed simultaneously with the above-described concave portion formation step S1-1 as illustrated in FIG. 15A. Specifically, the bending piece 117 is bent until coming into contact with a portion other than the bending piece 117 in the plate material 110. As a result, the concave portion 113 is formed in the outer edge 112 as described above, and a portion of the bending piece 117 of the plate material 110 has a two-layered stacked structure, and this portion serves as the above-described opening reinforcement portion 50 (see FIG. 2 and the like) when the needle member 10 is completed.

The concave portion formation step S1-1 and the opening reinforcement portion formation step S1-2 are executed simultaneously in the present embodiment in this manner, but may be configured as steps that are executed separately in different procedures. However, if the concave portion formation step S1-1 and the opening reinforcement portion formation step S1-2 are executed simultaneously as in the present embodiment, it is possible to reduce the number of steps and to enhance the work efficiency at the time of manufacturing the needle member 10.

In the tubular shape pressing step S1-3 of the tubular body providing step S1 of the present embodiment, the plate material 110 is placed in a press-molding machine 202, and the plate material 110 is deformed into a tubular shape by an upper die 202a and a lower die 202b of the press-molding machine 202 as illustrated in the drawing depicted on the right of the lower part of FIG. 15A, the drawing depicted on the left of the upper part of FIG. 15B, the drawing depicted on the right of the upper part of FIG. 16 and the drawing depicted on the left of the middle part of FIG. 16. In the press-molding machine 202, a plurality of types of shapes are prepared as the upper dies 202a and the lower dies 202b, and the plate material 110 is pressed a plurality of times and gradually bent to be deformed into the tubular shape while appropriately changing a combination of the upper die 202a and the lower die 202b.

In addition, the tubular body 114 is provided by welding or bonding the portion of the joint X of the plate material 110 deformed into the tubular shape in the above-described tubular shape pressing step S1-3 in the joining step S1-4 of the tubular body providing step S1 of the present embodiment as illustrated in the drawing depicted on the left of the upper part of FIG. 15B and the drawing depicted on the right of the middle part of FIG. 16. Specifically, the outer edges 112 of the plate material 110 in which the concave portions 113 are formed are aligned to weld the joint X in the present embodiment.

The tubular body providing step S1 of the present embodiment includes the above-described concave portion formation step S1-1, opening reinforcement portion formation step S1-2, tubular shape pressing step S1-3, and the joining step S1-4, but the tubular body 114 may be provided using another step.

Next, the bending pressing step S2 of the present embodiment will be described. As illustrated in FIGS. 15B and 16, the bent portion projecting toward the hollow portion is formed over a predetermined range in a longitudinal direction of the tubular body 114 (the same direction as the longitudinal direction D in the state of the plate material 110 described above) by pushing the die from an outer surface of the tubular body 114 to press the tubular body 114 at a position, which opposes the opening portion 40 in the radial direction C of the tubular body 114, of the tubular body 114, in the bending pressing step S2 of the present embodiment. This bent portion serves as the above-described side wall reinforcement portion 30 (see FIGS. 5 to 7) when the needle member 10 is completed.

In the bending pressing step S2 of the present embodiment, the tubular body 114 is interposed between the upper die 202a and the lower die 202b of the press-molding machine 202 at the position opposing in the radial direction C, and a convex portion 203 formed on one of the upper die 202a and the lower die 202b (in the present embodiment, the convex portion 203 formed on the lower die 202b) is pushed against the outer surface of the tubular body 114, thereby forming the above-described bent portion. Thus, the tubular body 114 is deformed so as to expand in a direction orthogonal to an opposing direction of the upper die 202a and the lower die 202b by the bending pressing step S2, and there is a case where the tubular body 114 is deformed to a flat shape. In such a case, a correction step of returning the tubular body 114 to a substantially cylindrical shape may be performed after the bending pressing step S2.

Finally, the blade surface portion 115 is formed at one end portion of the tubular body 114, whereby the needle member 10 is completed as illustrated in the drawing depicted on the lower part of FIG. 15B. The sensor 1 can be manufactured by inserting the linear detection member 20 into the needle member 10.

Although the sensor 1 is completed by inserting the detection member 20 into the hollow portion 11 of the needle member 10 after the bent portion to serve as the side wall reinforcement portion 30 (see FIG. 5 and the like) is formed in the tubular body 114 to complete the needle member 10 in the method for manufacturing the needle member 10 illustrated in FIGS. 14 to 16, the bending pressing step S2 may be executed in a state where the detection member 20 is arranged inside the tubular body 114. In this manner, a shape of the bent portion can be formed in accordance with an outer surface shape of the detection member 20 located inside the tubular body 114, and it is possible to further enhance the position fixability of the detection member 20 in the completed sensor 1. In addition, the sensor 1 can be completed simultaneously with the completion of the needle member 10, and it is possible to improve the work efficiency at the time of manufacturing the sensor 1. Further, the sliding with an inner surface of the needle member 10 is reduced as compared to the case where the detection member 20 is inserted into the needle member 10 after the completion of the needle member 10, and thus, it is possible to prevent coating or the like of the detection member 20 from being damaged and peeled off.

In addition, the method for manufacturing the needle member 10 illustrated in FIGS. 14 to 16 may include another step such as a slope portion formation step of forming the above-described slope portion 19 (see FIG. 2 and the like), a polishing step, and a cleaning step in addition to the above-described three steps S1 to S3.

Figure 17A:
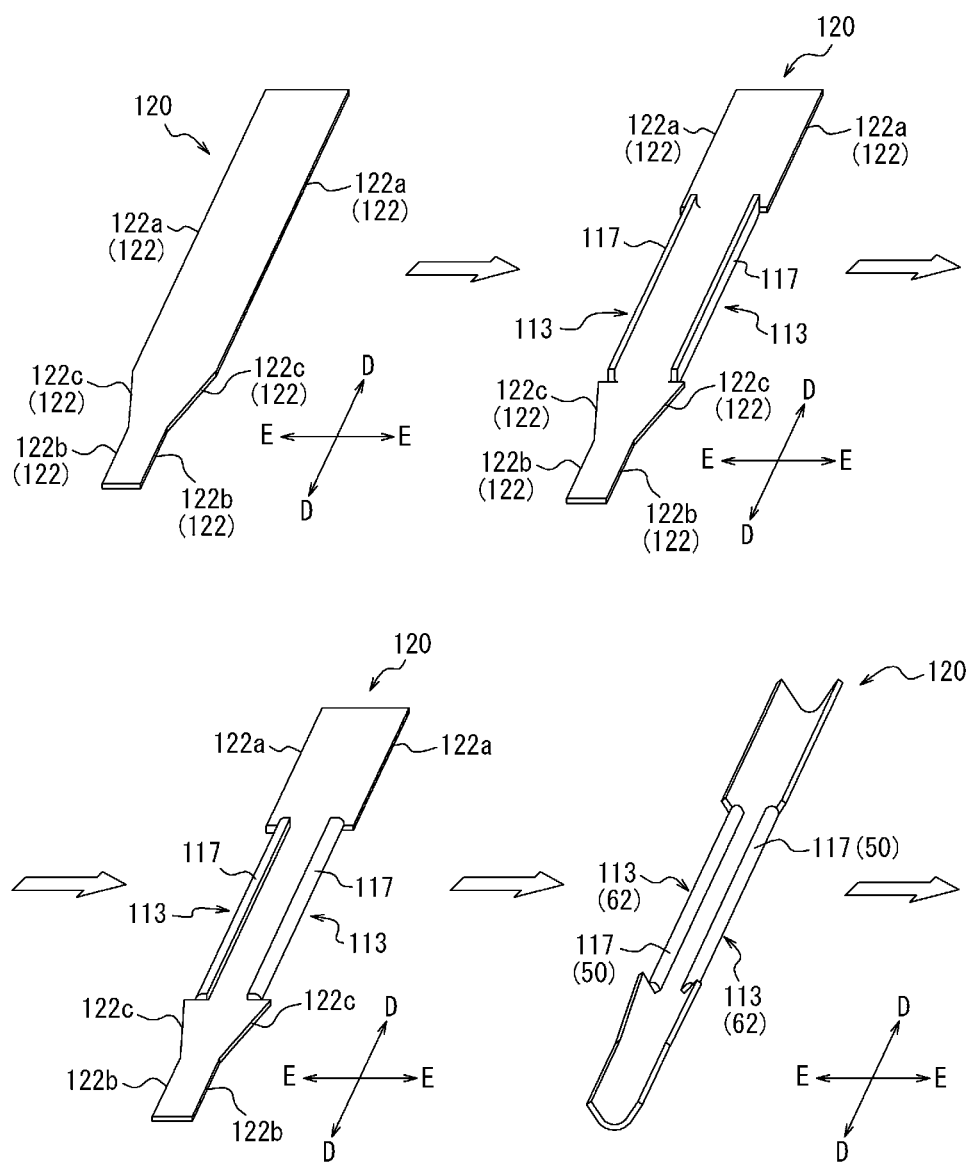
FIG. 17A is a schematic view illustrating an outline of a series of steps of a method for manufacturing the needle member illustrated in FIG. 8.
Figure 17B:
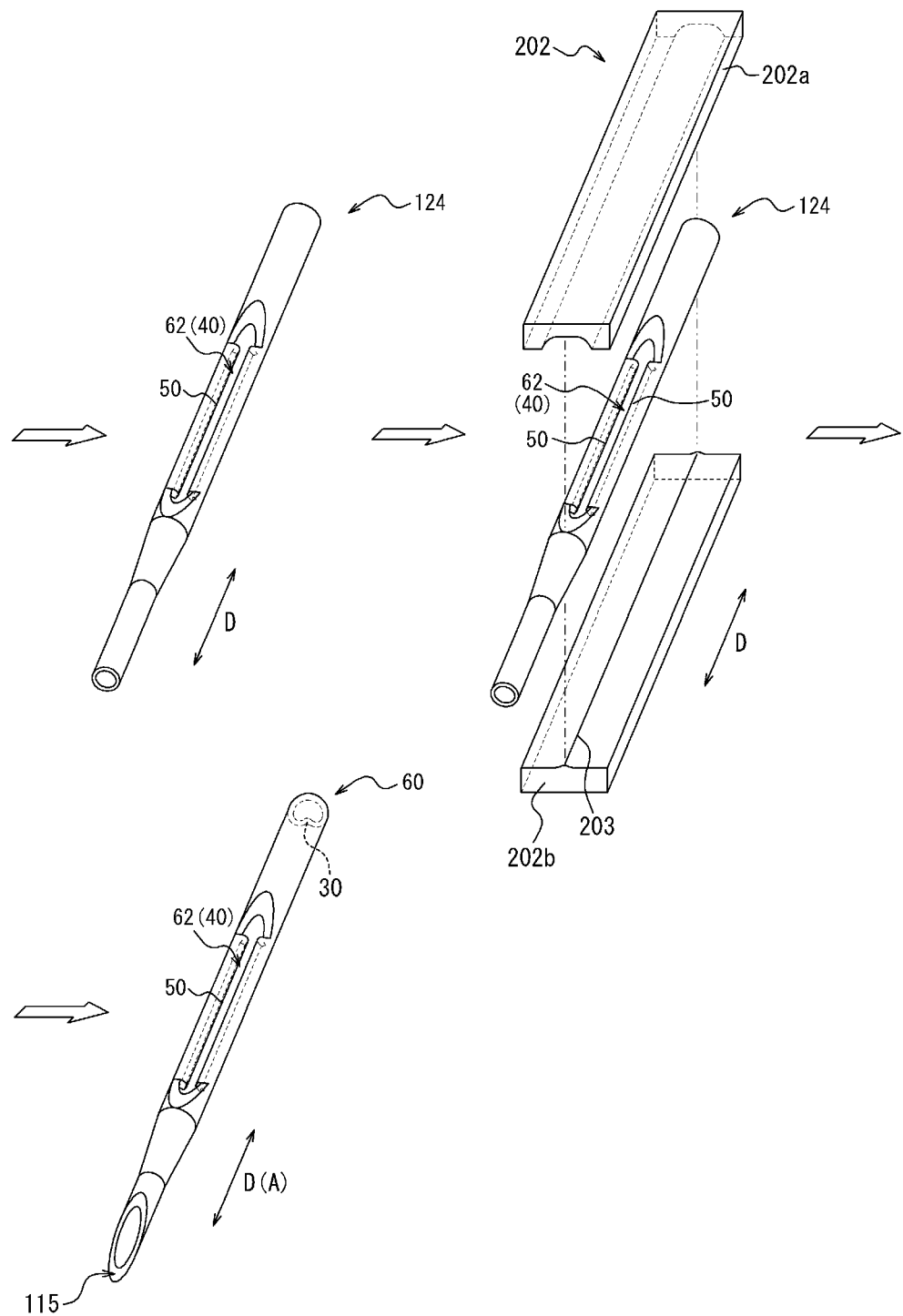
FIG. 17B is a schematic view illustrating a part of the series of steps in the method for manufacturing the needle member illustrated in FIG. 8.

Here, a method for manufacturing the needle member 60 illustrated in FIGS. 8 to 11 will be described. As an example of the method for manufacturing the needle member 60, the same method as the method for manufacturing the needle member 10 illustrated in FIG. 14 can be employed. FIGS. 17A and 17B are schematic views illustrating outlines of a series of steps S1 to S3 when the method for manufacturing the needle member 10 illustrated in FIG. 14 is applied as the method for manufacturing the needle member 60. As illustrated in FIGS. 17A and 17B, a tubular body 124 is formed using a plate material 120 including portions in which a length of a width in the lateral direction E is different so as to form the body portion 60a, the distal end portion 60b, and the tapered portion 60c (see FIGS. 8 to 11), respectively, when being deformed to the tubular body 124 in the method for manufacturing the needle member 60, instead of forming the tubular body 114 using the rectangular plate material 110 (see FIG. 15A). That is, outer edges 122 located on both sides in the lateral direction E of the plate material 120 are not straight, and a first outer edge portion 122a of the portion to form the body portion 60a, a second outer edge portion 122b of the portion to form the distal end portion 60b, and a third outer edge portion 122c of the portion to form the tapered portion 60c are continuous. The bending piece 117 is formed at a position of the first outer edge portion 122a. The other points are the same as those in the steps S1 to S3 in the method for manufacturing the needle member 10 illustrated in FIGS. 14 to 16, and thus, will not be described here.

In addition, the same manufacturing method as the method for manufacturing the needle member 10 illustrated in FIGS. 14 to 16 can be used, except for the tubular body providing step S1, regarding the method for manufacturing the needle member 70 illustrated in FIGS. 12 and 13. Specifically, the needle member 70 illustrated in FIGS. 12 and 13 is different from the above-described needle member 10 (see FIGS. 2 to 7 and the like) in terms of a configuration of the opening portion 40 and presence or absence of the opening reinforcement portion 50. Thus, the concave portion formation step S1-1, the opening reinforcement portion formation step S1-2, and the joining step S1-4 of the tubular body providing step S1 in the method for manufacturing the needle member 10 described above are not executed in the tubular body providing step S1 in the method for manufacturing the needle member 70 illustrated in FIGS. 12 and 13.

The needle member, the sensor, and the method for manufacturing the needle member according to the present disclosure are not limited to the specific configurations and processes described in the above embodiments, and various modifications, changes, and combinations can be made without departing from the scope of the claims. A tubular body that has an arbitrary diameter and in which an opening portion is formed in a side wall may be provided by an arbitrary tubular body providing step, and the needle member may be manufactured using this provided tubular body, instead of using the tubular body providing step S1 described in the above embodiment. Alternatively, the concave portion 113, which serves as the through-hole 40a when the tubular body 114 is formed, is formed in the plate material 110 in the method for manufacturing the needle member 10 illustrated by the above embodiment, but processing to form the through-hole 40a may be performed after forming the tubular body 114. In this case, it is preferable to employ a processing method in which heat is not applied. However, the concave portion 113 that serves as a base of the through-hole 40a can be formed in the series of steps of forming the tubular body 114 if the concave portion 113 is formed in the course of forming the tubular body 114 as illustrated in the above embodiment. Thus, it is unnecessary to separately execute post-processing only for formation of the through-hole 40a after formation of the tubular body 114, and it is possible to enhance the work efficiency in the manufacture of the needle member 10.

The present disclosure relates to a needle member, a sensor, and a method for manufacturing the needle member.

REFERENCE NUMERAL LIST 1 sensor
2 control unit
3 support member
4 housing
10 needle member
10a body portion
10b distal end portion
11 hollow portion
11a distal end opening
12 side wall
12a receiving groove
13a receiving surface
14 top portion
15 first side portion
16 second side portion
17 blade surface portion
17a blade surface
17b blade tip 18 edge portion
19 slope portion
19a first slope portion
19b second slope portion
20 detection member
30 side wall reinforcement portion
30a reinforcement portion inner surface
40 opening portion
40a through-hole
50 opening reinforcement portion
60 needle member
60a body portion
60b distal end portion
60c tapered portion
61 blade surface portion
62 through-hole
63 edge portion
64 side wall
70 needle member
71 slit
72 blade surface portion
72b heel portion
73 edge portion
100 measurement device
110 plate material
112 outer edge
113 concave portion
114 tubular body
115 blade surface portion
116 notch
117 bending piece
120 plate material
122 outer edge
122a first outer edge portion
122b second outer edge portion
122c third outer edge portion
124 tubular body
202 press-molding machine
202a upper die
202b lower die
203 convex portion
A extending direction of needle member
B circumferential direction of needle member
C radial direction of needle member
D longitudinal direction of plate material
E lateral direction of plate material
O longitudinal axis of needle member
W width of needle member
X joint
BS body surface of subject

The invention claimed is:

1. A sensor comprising:
a needle member comprising:
a tubular side wall through which a hollow portion extends in a longitudinal direction,
wherein an opening portion connected to the hollow portion extends laterally through the tubular side wall, and
wherein the tubular side wall comprises a side wall reinforcement portion located at a position opposing the opening portion, wherein the hollow portion is interposed between the opening portion and the side wall reinforcement portion; and
a linear detection member located in the hollow portion of the needle member; wherein:
the side wall reinforcement portion comprises a reinforcement portion inner surface that protrudes toward the hollow portion, the reinforcement portion inner surface comprising:
a top portion, and
a side portion that is continuous with the top portion;
an inner surface of the needle member defines a receiving groove that receives the detection member at a position adjacent to the reinforcement portion inner surface;
a distance from a longitudinal axis of the needle member to the inner surface of the needle member in a radial direction increases from the top portion toward a side of the needle member; and
the side portion comprises a portion of a receiving surface that receives the detection member.

2. The sensor according to claim 1, wherein:
an outer cross-sectional shape of the detection member is substantially circular; and
the receiving surface comprises a concave curved surface configured to contact a circumferential surface of the detection member.

3. A sensor comprising:
a needle member comprising:
a tubular side wall through which a hollow portion extends in a longitudinal direction,
wherein an opening portion connected to the hollow portion extends laterally through the tubular side wall, and
wherein the tubular side wall comprises a side wall reinforcement portion located at a position opposing the opening portion, wherein the hollow portion is interposed between the opening portion and the side wall reinforcement portion; and
a detection unit configured to detect a substance to be measured, the detection unit comprising an electrode layer or a reagent layer that is stacked on an inner surface of the needle member.

4. A method for manufacturing a needle member, the method comprising:
forming a tubular body having an opening portion formed in a side wall thereof by performing steps comprising:
forming a first concave portion at a first outer edge of a plate material, and forming a second concave portion at a second outer edge of the plate material, and
deforming the plate material into a tubular shape through which a hollow portion extends such that the first outer edge where the first concave portion is formed is aligned with the second outer edge where the second concave portion is formed; and
forming a bent portion that protrudes toward the hollow portion by pressing the tubular body at a position that opposes the opening portion in a radial direction of the tubular body.

5. The method for manufacturing a needle member according to claim 4, wherein the step of forming the tubular body further comprises forming a first opening reinforcement portion at a first edge portion that defines the first concave portion of the plate material, and forming a second opening reinforcement portion at a second edge portion that defines the second concave portion of the plate material.

* * * * *